United States Patent
Peleg (10) Patent No.: US 8,861,783 B1
(45) Date of Patent: Oct. 14, 2014

(54) SYSTEM AND METHOD FOR DETECTION OF CONTENT IN AN IMAGE STREAM OF THE GASTROINTESTINAL TRACT

(71) Applicant: Given Imagine Ltd., Yoqneam (IL)

(72) Inventor: Dori Peleg, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 27 days.

(21) Appl. No.: 13/729,263

(22) Filed: Dec. 28, 2012

Related U.S. Application Data (60) Provisional application No. 61/581,775, filed on Dec. 30, 2011.

(51) Int. Cl.
G06K 9/00 (2006.01)
H04N 7/18 (2006.01)

(52) U.S. Cl.
CPC .................................. *H04N 7/18* (2013.01)
USPC ....................................................... 382/100

(58) Field of Classification Search
None
See application file for complete search history.

(56) References Cited

U.S. PATENT DOCUMENTS

| | | | |
|---|---|---|---|
| 4,278,077 A | 7/1981 | Mizumoto | |
| 4,936,823 A | 6/1990 | Colvin et al. | |
| 5,604,531 A | 2/1997 | Iddan et al. | |
| 5,697,384 A | 12/1997 | Miyawaki et al. | |
| 5,993,378 A | 11/1999 | Lemelson | |
| 6,240,312 B1 | 5/2001 | Alfano et al. | |
| 7,009,634 B2 | 3/2006 | Iddan et al. | |
| 7,454,045 B2 | 11/2008 | Yao et al. | |
| 7,480,401 B2 | 1/2009 | Shen et al. | |
| 7,986,337 B2 | 7/2011 | Davidson et al. | |
| 2002/0103417 A1 | 8/2002 | Gazdzinski | |
| 2003/0167000 A1 | 9/2003 | Mullick et al. | |
| 2003/0190064 A1 | 10/2003 | Inoue | |
| 2003/0208107 A1 | 11/2003 | Refael | |
| 2005/0075537 A1 | 4/2005 | Chen et al. | |
| 2005/0078858 A1 | 4/2005 | Yao et al. | |
| 2006/0074275 A1 | 4/2006 | Iddan et al. | |
| 2006/0164511 A1 | 7/2006 | Krupnik | |
| 2006/0247514 A1 | 11/2006 | Panasyuk et al. | |
| 2007/0024946 A1 | 2/2007 | Panasyuk et al. | |
| 2007/0078300 A1 * | 4/2007 | Zinaty et al. ................. | 600/102 |
| 2007/0078335 A1 | 4/2007 | Horn | |
| 2009/0244260 A1 | 10/2009 | Takahashi et al. | |
| 2009/0284589 A1 * | 11/2009 | Radeva et al. ................. | 348/77 |

OTHER PUBLICATIONS

Malatras, Pervasive Computing and Communications Design and Deployment: Technologies, Trends, and Applications, May 2011, Information Science Reference, pp. 42-43.*
U.S. Office Action for U.S. Appl. No. 11/239,392 dated Oct. 27, 2009.

(Continued)

*Primary Examiner* — Stephen R Koziol
*Assistant Examiner* — Raphael Schwartz
(74) *Attorney, Agent, or Firm* — Pearl Cohen Zedek Latzer Baratz LLP (57) ABSTRACT

A system and method for detecting in-vivo content includes an in-vivo imaging device for capturing a stream of image frames in a GI tract, a content detector for detecting and/or identifying one or more image frames from the stream of image streams that may show substantially only content, a display selector to remove detected frames from the image stream, and a monitor to display the remaining image frames as a reduced image stream.

18 Claims, 4 Drawing Sheets

(56) References Cited

OTHER PUBLICATIONS

U.S. Office Action for U.S. Appl. No. 11/239,392 dated May 6, 2010.
U.S. Office Action for U.S. Appl. No. 11/239,392 dated Jul. 5, 2011.
U.S. Office Action for U.S. Appl. No. 11/239,392 dated Dec. 15, 2011.
U.S. Office Action for U.S. Appl. No. 11/239,392 dated Jun. 19, 2012.
U.S. Office Action for U.S. Appl. No. 11/239,208 dated Aug. 16, 2007.
U.S. Office Action for U.S. Appl. No. 11/239,208 dated Dec. 27, 2007.
U.S. Office Action for U.S. Appl. No. 11/358,292 dated Aug. 17, 2007.
U.S. Office Action for U.S. Appl. No. 11/358,292 dated Dec. 28, 2007.
U.S. Office Action for U.S. Appl. No. 11/358,292 dated Oct. 29, 2008.
Tjoa, M.P. Krishnan, S. M., "Feature extraction for the analysis of colon status for the endoscopic images", Biomed Eng. Online. 2003; 2:9 9, Apr. 8, 2003, doi: 10.1186/1475-925X-2-9.
Kang, J., Doraiswami, R., "Real-time image processing system for endoscopic applications", Electrical and Computer Engineering, 2003. IEEE CCECE 2003. Canadian conference on, May 4-7, 2003, vol. 3, on pp. 1469-1472 vol. 3 ISBN:0-7803-7781-8.
Chindaro, S., Sirlantzis, K., Devari, F., "Colour space fusion for texture recognition", Video/Image Processing and Multimedia Communications, 2003. $4^{th}$ EURASIP Conference focused on, Jul. 2-5, 2003, vol. 1, on pp. 181-186 vol. 1, ISBN: 935-184-154-7.

\* cited by examiner

SYSTEM AND METHOD FOR DETECTION OF CONTENT IN AN IMAGE STREAM OF THE GASTROINTESTINAL TRACT

PRIOR APPLICATION DATA

The present application claims the benefit of prior provisional application Ser. No. 61/581,775, filed on Dec. 30, 2012, incorporated by reference herein in its entirety.

FIELD OF THE INVENTION

The present invention relates to a method and system for image processing of an image stream captured in-vivo. More specifically, the present invention relates to systems and methods for detecting intestinal content in an image stream of the gastrointestinal tract.

BACKGROUND OF THE INVENTION

In-vivo imaging methods, such as performed by an in-vivo imaging system including an ingestible capsule, may be used to image body lumens within a patient. The imaging system may capture and transmit, for example, images of the gastrointestinal (GI) tract to an external recording device, while the capsule passes through the GI lumen. The capsule may capture images in variable frame rates of, for example, 2-40 frames per second. Large numbers of images, for example 100,000 to 300,000 images, may be collected for viewing during the imaging procedure, and may also be viewed and/or processed in real time. The images may be combined in sequence, and an image stream or movie of, for example, 30-120 minutes in length, may be presented to a user.

The capsule may collect data from different points along a body lumen, for example lumens of the GI tract, and transmit the data externally for analysis and diagnosis. The GI tract is a very long and curvy path which usually includes GI content. Content within the body lumen may be any fluid, solid, liquid, gas, particle, feces, bile, or any substance that is not a permanent or stagnant substance within the body lumen.

U.S. Patent Application Publication No. 2007/0078300, issued as U.S. Pat. No. 7,567,692, assigned to the common assignee of the present application, discloses a system and method for detecting in-vivo content. The system may include in some embodiments an in-vivo imaging device for capturing a stream of image frames in a GI tract, a content detector for detecting and/or identifying one or more image frames from the stream of image streams that may show content, and a graphical user interface (GUI) to display image frames detected.

SUMMARY OF THE INVENTION

Embodiments of the present invention include a system and computer-implemented method for detecting intestinal content in in-vivo images. A stream of in-vivo images may be received from an in vivo imaging capsule, and at least one image from the stream may be selected for intestinal content analysis.

In some embodiments, the method may be used to select images from an image stream and present the selected images to a user. For example, the selected images may include images which are not completely obscured by intestinal content. Non-selected images may include images which have a certain probability, for example a low probability, of containing visible pathology. The selected images may include images which have a certain probability, for example a high probability, of containing a non-obscured region of the image.

In some embodiments, a method may be used to select pathological images which substantially do not depict or represent intestinal contents.

In an embodiment of the present invention, a method for detecting in-vivo content in images captured by an in vivo imaging capsule may include receiving an in vivo image captured by the imaging capsule, calculating a pixel content score or pixel probability per pixel (e.g., for each pixel), for at least a subset of the image pixels and calculating an image content score based on the pixel content scores. The pixel content score may indicate or correspond to a probability or may be a probability that the pixel depicts or represents in-vivo content (e.g., the pixel is part of a section of image showing, depicting or representing in-vivo content). The image content score may indicate a probability that an image represents or depicts more (or equal to or more) intestinal content than, for example, a content amount threshold or a selected content amount threshold. Other pixel content scores and image content scores may be used. The content amount threshold may be as a percentage or portion of pixels in an image (or a portion of an image) which depict content, or as an area of an image which depicts content. In some embodiments, the content amount threshold may be the number of pixels in the image (or in a subset region of the image) which depict content. Other thresholds may be used.

The image content score may be calculated by selecting a pixel content score or probability (e.g. from the calculated pixel content scores), which corresponds to a content amount threshold percentile.

Images from an original image stream captured in vivo may be selected according to the image content scores, for display in a reduced image stream (e.g., a subset of the images captured by the in-vivo imaging device, where the number of images in the subset is reduced from the original image stream captured by the imaging device). The reduced image stream of in vivo images may be displayed to a user, for example on a monitor of a computer, laptop, personal digital assistant (PDA), mobile telephone, etc. In some embodiments, the content amount threshold may be determined based on a probability of an image to include visible pathology. The method may include calculating an image stream content rating, and displaying the content rating to a user.

In some embodiments, the pixel content score may be calculated based on red, green and blue components of each pixel.

A training set of marked images may be received, for example by a processing unit which may execute a linear or non-linear classifier. The classifier may be trained according to the training set. The images may include pixels which are marked (or classified) as content pixels and/or pixels which may be classified as tissue pixels. Other classes may be used. The classifier may be trained to provide a pixel content score based on the training set of images.

A system for detecting in-vivo content in images may be provided according to embodiments of the present invention. The system may include an imaging device to capture an in vivo image stream, a storage unit to store the image stream, a processing unit to receive a plurality of images from the image stream, and for each image to calculate a pixel content score for at least a subset of image pixels, and to calculate an image content score. The image content score may be calculated based on a percentile of the pixel content score corresponding to a content amount threshold. The processing unit may select images from the stream for display as a reduced or shortened stream, according to the image content scores. The system may include a monitor or screen to display the selected images of the image stream to a user.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIG. 4 illustrates an exemplary graph of a ROC (Receiving Operator Characteristic) curve generated for a content detector according to an embodiment of the invention It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Devices according to embodiments of the present invention, including imaging, receiving, processing, storage and/or display units suitable for use with embodiments of the present invention, may be similar to embodiments described in US Patent Application Publication Number 2006/0074275, entitled "SYSTEM AND METHOD FOR EDITING AN IMAGE STREAM CAPTURED IN-VIVO", issued as U.S. Pat. No. 7,986,337, U.S. Pat. No. 5,604,531 to Iddan et al., entitled "In-vivo Video Camera System", and/or in U.S. Pat. No. 7,009,634 to Iddan et al., entitled "Device for In-Vivo Imaging", each assigned to the common assignee of the present application. Of course, devices and systems as described herein may have other configurations and other sets of components. Devices, systems and methods according to some embodiments of the present invention may incorporate or be adapted from the commercial PillCam® SB2 or PillCam® Colon capsules and the associated data recorders and RAPID® workstation provided by Given Imaging Ltd.

In embodiments of the present invention, a system, and method may detect turbid content in in-vivo image frames, for example by providing a system, and method for automatically identifying, detecting, selecting, and marking image frames captured in the GI tract that may depict or represent the presence of turbid content. Analysis of the transmitted data may be used to automatically and/or machine select and mark image frames that may depict or show gastrointestinal turbid content and thus which may include pixels which themselves depict or show content. Analysis and processing of the data may be performed automatically by a processing device, without user intervention. Machine selection, detection and/or marking of image frames that may depict content or may be candidates for content identification may be performed at least partially by a content detector and such that user intervention in the detection of image frames that may be candidates for content identification may not be required. Machine selection, detection and/or marking may be performed by, for example, one or more processors, a workstation, circuitry, a sensor or any other computation and/or sensing able device. According to some embodiments of the present invention, selected images may be displayed to a health professional for diagnosis. In some embodiments of the present invention, screening may also be facilitated with data that may be partially occluded by content. For example, image frames may be captured in an environment that may be partially occluded with content, for example content that may be present within a body lumen, e.g. small bowel or colon.

In one embodiment, the selected image frames may be removed or excluded from the image stream, in order to display to a health professional a stream of images which are not occluded by in vivo turbid content. In some embodiments, the selected image frames may be counted, and the number or percentage of excluded images (from the total number of images originally captured by the imaging device) may be displayed to a health professional as a measure for diagnosis. Other embodiments allow displaying the detected images within the image stream, or alternately, to display only the detected images.

Gastrointestinal content in an in-vivo lumen may include any fluid, solid, liquid, gas, particle, feces, bile, chyme, semi-fluid paste, mucus or any substance that is not a permanent or stagnant substance within the body lumen. An in vivo imaging capsule capturing images within a body lumen which contains intestinal juices or remains of food may produce turbid frames, which may prevent or hinder correct visualization of the in-vivo tissue. Turbid image frames may include images depicting a certain amount of gastrointestinal content. In some cases, pathologies may appear in image frames which depict content as well. For example, an area of 95% of the image or 95% of a selected portion of an image may be covered with turbid content, however the remaining area of the image or portion thereof (e.g. 5%) may depict a pathology. In such cases, it may be desirable to keep the image and display it to the health professional reviewing the imaging procedure, since it is desirable not to exclude an image depicting pathology from the displayed image stream. Different amounts or percentages of turbid content in the images may be set to determine whether an image frame is considered a turbid frame or not.

Figure 1:
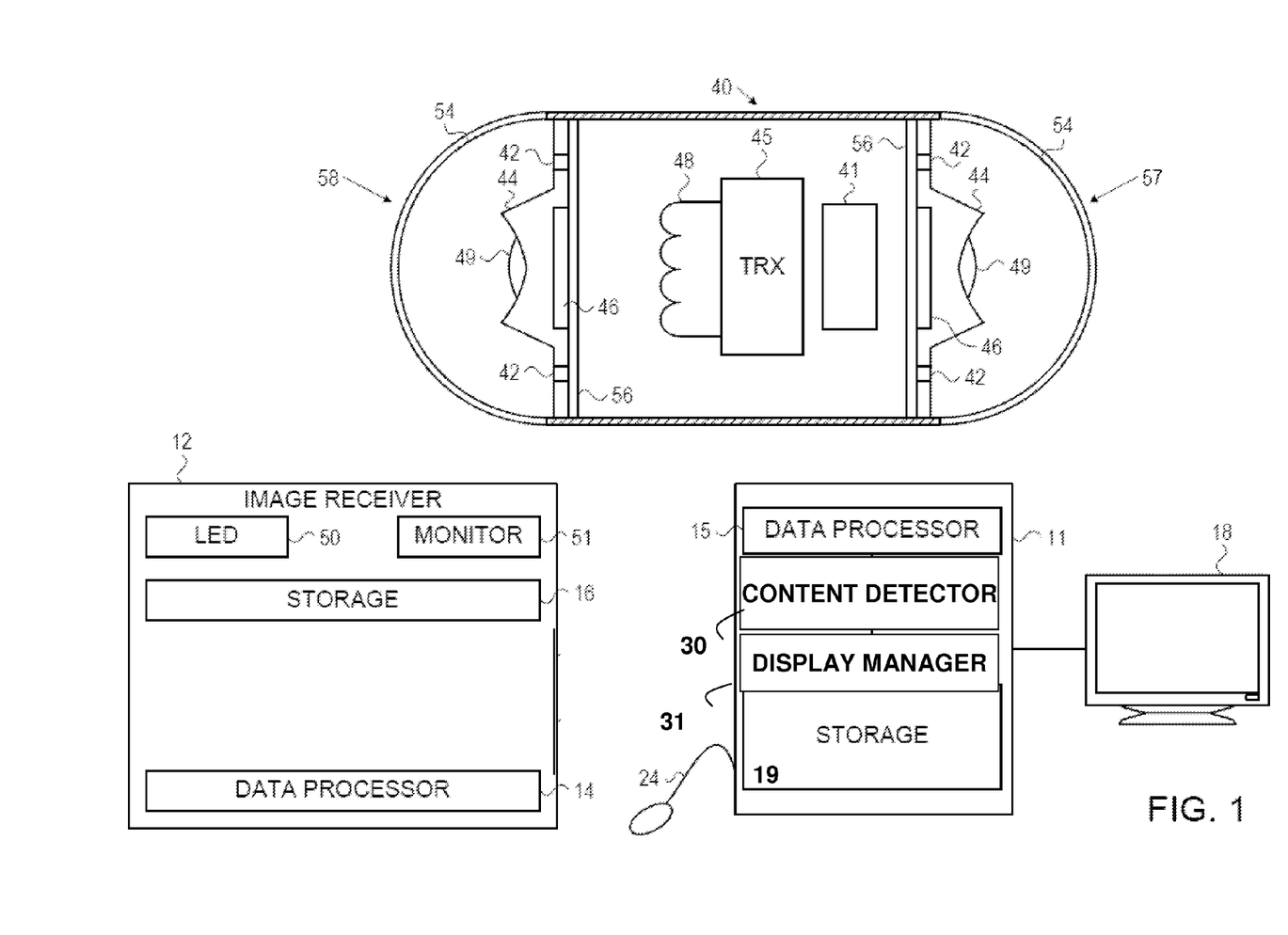
FIG. 1 shows a schematic diagram of an in-vivo imaging system according to an embodiment of the present invention.

Reference is made to FIG. 1, which schematically illustrates an in-vivo imaging system according to an embodiment of the invention. According to some embodiments, the system may include a device, for example, a capsule 40. Capsule 40 may be a swallowable in-vivo capsule, but other sorts of devices or suitable implementations may be used. According to one embodiment, capsule 40 may communicate with an external receiving and display system to provide display of data, control, or other functions. For example, power may be provided by an internal battery 41 or a wireless receiving system. Other embodiments may have other configurations and capabilities.

Capsule 40 may include one or more imager(s) 46 for capturing images, one or more illumination sources 42 for illuminating the body lumen, and a transmitter 45 for transmitting image data and possibly other information to a receiving device such as receiver 12. Transmitter 45 may include receiver capability, for example, to receive control information. In some embodiments, the receiving capability may be included in a separate component. An optical system, including, for example, lenses 49, lensholders 44 or mirrors, may aid in focusing reflected light onto the imagers 46. The lenholders 44, illumination units 42, and imagers 46 may be mounted on a substrate 56. An imaging head 57 and/or 58 may include the optical system, optical dome 54, imager 46, illumination units 42, and substrate 56.

Preferably, located outside the patient's body in one or more locations, are an image receiver 12, preferably including an antenna or antenna array, an image receiver storage unit 16, one or more data processors 14, 15, a data processor storage unit 19, and an image monitor 18, for displaying, for example, the images recorded by the capsule 40. Preferably, the image receiver 12, data processor 14 and image receiver storage unit 16 are small and portable, and are worn on the patient's body during recording of the images. The data processor 15, data processor storage unit 19, and image monitor 18 may be included in a computer or workstation 11, or may be included in the image receiver.

According to embodiments of the present invention, data processor 14 may receive images and telemetry data received by image receiver 12, for example in real time, or with a minimal delay. According to one embodiment of the invention, data processor 15, data processor storage unit 19 and monitor 18 may be part of a personal computer or workstation 11 which includes standard components such as a processor, a memory, a disk drive, and input-output devices, although alternate configurations are possible, and embodiments of the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 15.

Data processors 14 and 15 may include one or more standard data processors, such as a microprocessor, multiprocessor, accelerator board, or any other serial or parallel high performance data processor. Image monitor 18 may be a computer screen, a conventional video display, or any other device capable of providing image or other data. In some embodiments, an image and/or text display 51 may be provided in image receiver 12, in addition to or instead of image monitor 18. Data processors 14 and 15 may perform methods as disclosed herein by executing software or instructions stored, for example, in storage 16 or 19.

Data processor storage unit 19 may store a series of images recorded or captured by a capsule 40. The images the capsule 40 records as it moves through a patient's GI tract may be combined consecutively to form a moving image stream or movie.

While, preferably, information gathering, storage and processing are performed by certain units, a system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

Preferably, the imager 46 is a suitable complementary metal-oxide-semiconductor (CMOS) camera, such as a "camera on a chip" type CMOS imager specified by Given Imaging Ltd. of Israel and designed by Aptina Corporation of California, USA. In alternate embodiments, the imager 46 may be another device, for example, a charge-coupled device (CCD). The illumination source 42 may be, for example, one or more light emitting diodes, or another suitable light source.

During an in vivo imaging procedure, imager 46 may capture images and send data representing the images to transmitter 45, which transmits images to image receiver 12 using, for example, electromagnetic radio waves. Image receiver 12 may transfer the image data to image receiver storage unit 16. In some embodiments, image data stored in storage unit 16 may be sent and processed immediately, e.g. in real time or substantially in real time, in the data processor 14. In other embodiments, after a certain period of time of data collection, the image data stored in storage unit 16 may be sent to the data processor 15 or the data processor storage unit 19. For example, the image receiver storage unit 16 may be taken off the patient's body and connected to the personal computer or workstation which includes the data processor 15 and data processor storage unit 19 via a standard data link, e.g., a serial or parallel interface of known construction. In some embodiments, the data captured by the capsule may be stored in a storage unit located within the capsule, and may be extracted from the capsule at a later time, for example after the procedure is completed.

Data processor 14 may analyze the data, and may store the result, for example per image. Data processor 14 may execute or operate software or code (e.g., stored in storage 16) which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, manipulated or analyzed. A health professional may use the images to diagnose pathological conditions of, for example, the GI tract, and in addition, the system may provide information about the location of these pathologies. While using a system where the data processor storage unit 19 first collects data and then transfers data to the data processor 15, the image data is not viewed in real time. When using a system in which data processor 14 receives the data by data receiver 12 and processes or partially processes immediately (e.g., substantially upon image receipt, the image may be processed), real time or quasi-real time viewing is possible.

According to one embodiment, the capsule 40 may collect a series of still images as it traverses the GI tract. The images may be later presented as, for example, a stream of images or a moving image of the traverse of the GI tract. One or more in-vivo imager systems may collect a large volume of data, as the capsule 40 may take several hours to traverse the GI tract. The imager(s) 46 may record images at a rate of, for example, two to forty images per second each (other rates, such as four frames per minute, may be used). The imager(s) 46 may have a fixed or variable frame capture and/or transmission rate. When the imager(s) 46 have a variable or adaptive frame rate (AFR), the imager(s) 46 may switch back and forth between frame rates, for example, based on parameters, such as the capsule 40 speed, its estimated location, similarity between consecutive images, or other criteria. Thousands of images, for example, over 300,000 images, may be recorded. The image recordation rate, the frame capture rate, the total number of images captured, the total number of images selected for the edited moving image, and the view time of the edited moving image, may each be fixed or varied.

Preferably, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19 and/or in image receiver storage unit 16. The stored data may include one or more pixel properties, including color and brightness values.

According to an embodiment of the invention, the data processor 15 may include or execute a content detector 30 for determining a content score for an image. Content detector 30 may be a content detection processor and may be implemented for example by data processor 15 executing code or software, e.g., stored in storage unit 19. While the content detector is shown in FIG. 1 as being separate from and connected to processor 15, in some embodiments content detector 30 may be a set of code or instructions executed by, for example, processor 15 (or another processor such as processor 14). Content detector 30 may be or may include one or more dedicated processors. The content detector 30 may evaluate the degree or occurrence in each image frame of qualities based on each of a plurality of pre-defined criteria, defined for example in the content detector 30 or in a separate storage unit. For example, the content detector 30 may process the images and/or the telemetry data, and determine, for example in real time or after pre-processing of the image stream, whether images or portions thereof depict a certain level of gastrointestinal content.

In some embodiments, a classification process based on a series of operations and pre-defined criteria may be used to determine a content score for a captured image. The content score may be a rating, or measure which may be calculated for each image or for a selected subset of images from the in vivo image steam, which may indicate or correspond to a probability that the image depicts a certain level of content. For example, in some embodiments, images for processing by content detector 30 may be selected from a number of consecutive images (e.g., only one of every 5 images from the image stream may be processed) or from a set of images received within a predetermined time period (e.g. 1 minute). In some embodiments, content detector 30 may generate a simplified representation (e.g., a derived value or rating, such as an integer 0-100) of more complex characteristics of an image or a portion of an image (e.g., criteria, such as, color variation, appearance of certain textural or structural patterns, light intensity of the image or portions thereof, etc.). A score may include any rating, rank, hierarchy, scale or relative values of features or criteria. Typically a score is a numerical value, for example, a number from 1 to 10, but need not be limited as such. For example, scores may include, for example, letter (A, B, C, . . . ), signs or symbols (+, −), computer bit values (0, 1), the results of one or more decisions or conditions (yes, no), for example, indicated by the status of one or more computing flags. Scores may be discrete (non-continuous) values, for example, integers, a, b, c, etc., or may be continuous, for example, having any real value between 0 and 1 (subject to the precision of computer representation of numbers). Any interval between consecutive scores may be set (e.g., 0.1, 0.2, . . . , or 1, 2, . . . , etc.) and scores may or may not be normalized.

Scores for each frame or one or more portions thereof may be stored with the frames in the same database (e.g., image receiver storage unit 16). The scores may be defined, e.g., in a header or summary frame information package, for example with the data in an initial image stream. Alternatively or additionally, the scores may be stored in a database separate from the images with pointers pointing to the images.

Figure 3:
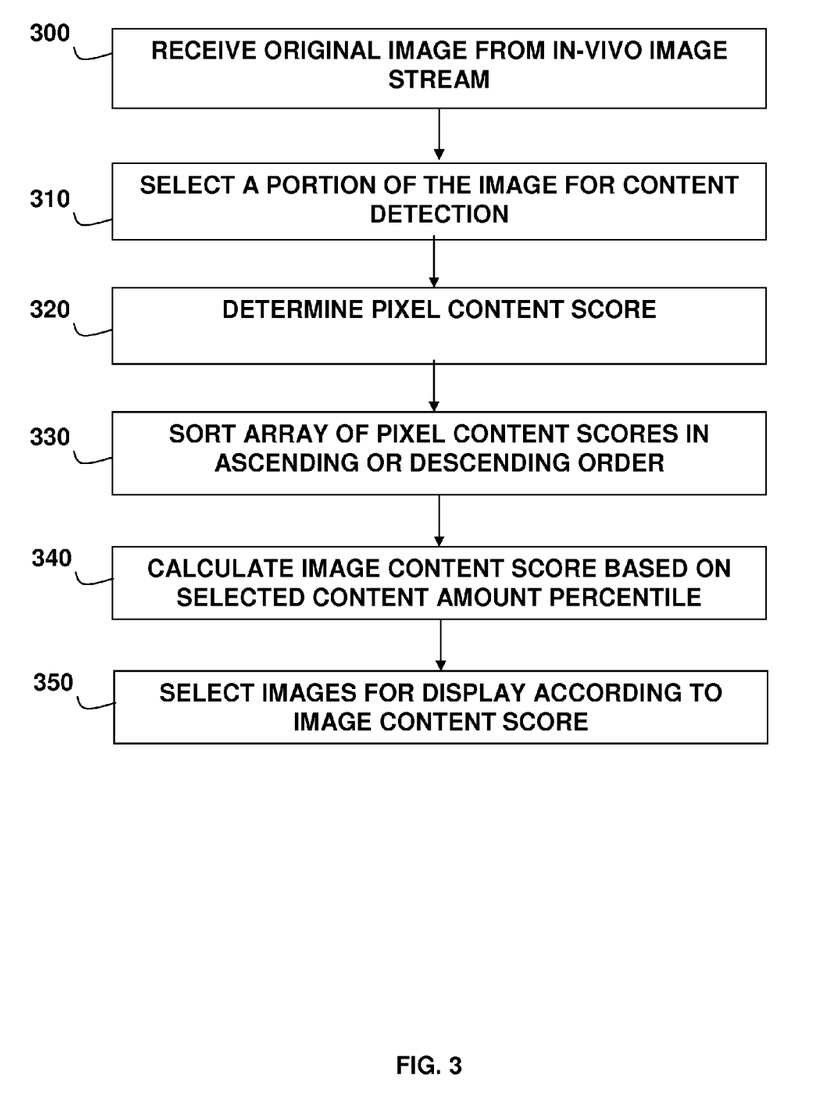
FIG. 3 is a flowchart of a method for selecting images for display, according to an embodiment of the present invention.

In one embodiment, content detector 30 may assign one or more combined scores, e.g., a scalar values or an average or combined values, rating each frame or group of frames based on predetermined criteria or steps, for example as described in FIG. 3. In some embodiments, content detector 30 may assign a content score to the image. The image content score may indicate (or correspond to) a probability or a confidence level that the image depicts a certain (e.g. predetermined) level (e.g. a percentage or area in of content depicted in the image, or a number of pixels classified as content pixels in the image) of turbid intestinal content. For example, the image content score may indicate a probability or a confidence level that the amount of intestinal content in the image is depicted in 95% or more pixels in the image. In some embodiments, if an image depicts mostly content or at least a predetermined level of content (e.g., 95% or more of the image is obscured by turbid content) the image content score assigned to the image will be a high score.

In images which depict substantially only turbid content, the in vivo tissue depicted in the image may not be visible or may not be clearly visible. Such images may have a relatively low clinical value, since the in vivo tissue may not be properly viewed or examined by a health care professional. In some embodiments, it may be useful to remove such images from the image stream displayed to the user, in order to reduce the number of images and the viewing time of the stream, and to assist the health care professional in focusing on images which may be clinically important or significant. A display manager 31 may be used to remove images which have a high probability of depicting a substantial amount of intestinal content from the image stream displayed to a user, or to skip such images when displaying the image stream. In some embodiments, the assigned score may indicate the amount of pixels in the image being occluded by turbid content, e.g. if half of the image is obscured by turbid content, the score may be 0.5 on a scale of zero to one. Other scales and thresholds may be used.

More than one content-related score may be calculated for an image, and used to determine whether to display the image to a viewer. For example, an image content score may indicate the probability of the image depicting a certain amount of content. An image content amount score may indicate the level or amount of content obscuring the image (or a selected portion of the image). These scores and/or other scores may be used when determining which images to remove from the image stream displayed to a user. In some embodiments, the image content score may be calculated based on content scores of each pixel or a subset of pixels in the image. For example, a pixel content score or pixel probability may be, indicate or correspond to a probability or a level of confidence that the pixel is a turbid content pixel, or a probability that the pixel is a tissue pixel, or that the pixel represents or depicts in-vivo content. Other pixel content scores and image content scores may be used.

In some embodiments the image content score may be calculated on a portion of the image. The image content score may indicate a probability that an image depicts more (or equal to or more) intestinal content than, for example, a content amount threshold or a selected content amount threshold. For example, a predetermined region of the image may be used, which contains a subset of pixels in the image. In some embodiments, the predetermined region of the image may be a Region of Interest (ROI) which may be used for other image processing tasks as well. Using the predetermined region for calculation of content scores may reduce calculation time per image, since regions of the image which are not useful to the viewer (e.g. due to optical distortion or insufficient illumination) are not used for calculation of the content score, and therefore do not consume processing resources.

The scores or measures may be absolute or relative to each other, and may be calculated based on a sequence of frames or on a single frame. The absolute score(s) for each frame or portion of frame may be a value associated with the criteria for the single frame. The relative score(s) for each frame or for a portion of frame may be, indicate, or be calculated based on a change in the value associated with the criteria relative to the value associated with the criteria for a previous or adjacent frame. Both absolute and relative scores may or may not be scaled (e.g. normalized). Scores may be scaled with a different scaling factor, for example, for images captured in different frame capture rates.

According to one embodiment, content detector 30 may process images or portions of images from one or more image streams captured by one or more imagers 46. For example, a double-headed capsule 40 may capture two image streams using two separate optical systems. The received image streams may be processed separately. For example, each stream may be processed as a separate stream, and for each image content detector 30 may determine independently one or more content scores. In other embodiments, streams may be merged. For example images from two or more streams may be sorted chronologically according to the capture time of the images and merged into a single stream, then processed as a single image stream. Other sorting or merging methods may be used, for example based on different image parameters such as similarity between images, or based other scores assigned to the images by different filters, or detectors (e.g. pathology or abnormality detectors). In some embodiments, images may be processed simultaneously, for example using more than one processor in parallel processing.

A region of interest may be predetermined in the image frames, for example a region which includes a subset of pixels from the total amount of pixels which the imager captures. The area outside the region of interest may include, for example, pixels which are out of focus due to optical properties of the imaging device, or pixels which are insufficiently illuminated due to illumination properties of the imaging device. For example, the region of interest of a square image may include only pixels within a circle which may be delimited by the square borders of the image.

Pathological tissue may appear in image frames which also contain turbid content. Different amounts or percentages of turbid content in the images may be determined and used as a turbidity percentile by content detector 30. In one example, an area of 95% of the image (or a region of interest within the original image) may be covered with turbid content, however the remaining area of the image (e.g. 5% of the image or 5% of a region of interest in the image) may depict a pathology. In such cases, it may be desired to keep the image and display it to the health professional reviewing the imaging procedure, since any image depicting pathology should not be excluded from the displayed image stream.

The display manager 31 may be implemented by data processor 15 executing code or software, e.g., stored in storage unit 19. While the display manager 31 is shown in FIG. 1 as being separate from and connected to processor 15, in some embodiments display manager 31 may be a set of code or instructions executed by, for example, processor 15 (or another processor such as processor 14). Display manager 31 may be or may include one or more dedicated processors, or may be implemented as part of other processing functions in the system, for example as part of content detector 30. In one example, based on the image content scores calculated by content detector 30, display manager 31 may determine which images from the input image stream to present to a viewer, and which images from the original image stream to exclude, skip or delete from the displayed moving image stream or movie.

In some embodiments, the display manager 31 may receive a stream of images and their corresponding image content scores (one or more content scores per image may be received). Display manager 31 may select images for display in a reduced stream, for example by marking images or tagging images which have image content scores that fulfill a predetermined condition. In one embodiment, the content scores of the selected images may be at or above or above a specific (predetermined) threshold. If more than one type of score is received per image, each type of score may be checked to determine of it fulfills a certain condition, for example a predetermined condition. In some embodiments, the condition may be calculated, e.g. based on image properties, properties of one or more previous images, and/or input from a user.

In some embodiments, a user may determine the condition's which should be satisfied for excluding images from the original stream. The user may select an amount or percentage of images which should be discarded or excluded from the original image stream. For example, a user may input a value of 10% of the images to be excluded by content detection. Accordingly, display manager 31 may select to discard 10% of the images from the original image stream which have the highest probability of being content images. In another example, a user may select to view only images which have more than 80% tissue pixels in them. Accordingly, display manager 31 may select to discard images which have more than 20% of the pixels classified as content pixels. Other conditions may be provided, for example as part of a Graphic User Interface which allow the user to select from a set of conditions or thresholds. In some embodiments, the conditions and thresholds may be predetermined and stored, for example in a storage unit (e.g. storage unit 19) which may be operationally connected to the display manager 31.

In some embodiments, the image (or pixel) content scores may be used by other image processing operations which may be performed on images of the stream. For example, the content scores may be used by other filters which may be used to reduce the number of images in the image stream displayed to a viewer. U.S. Pat. No. 7,986,337 to Davidson et al., assigned to the common assignee of the present application and incorporated herein by reference in its entirety, discloses in some embodiments a system and method for editing of an image stream produced by an ingestible capsule. The display manager 31 may include, for example, a set of predefined criteria, e.g. in addition to content detector 30, which may be used for editing the image stream to produce a shortened or reduced image stream.

Figure 2:
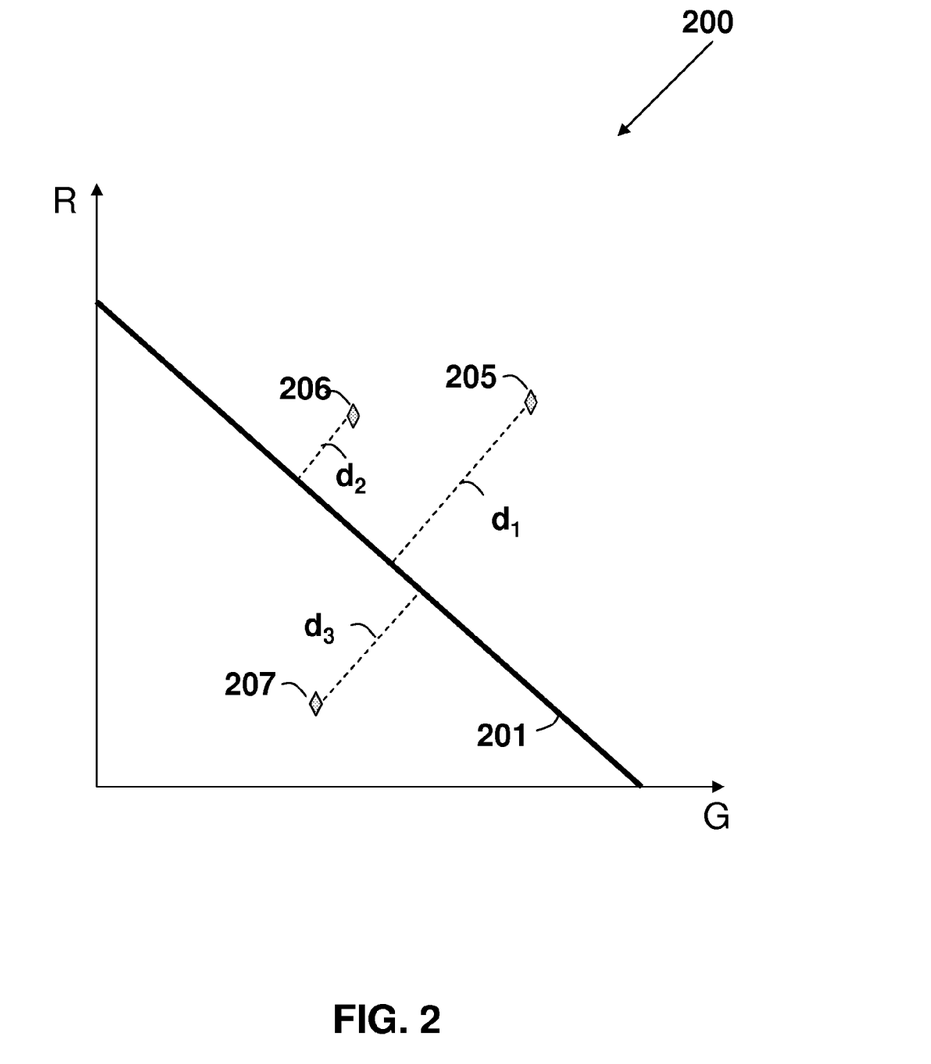
FIG. 2 depicts an example of a linear classification separator which may be used in an embodiment of the present invention.

Reference is now made to FIG. 2, which depicts an example of a linear classification separator which may be used in an embodiment of the present invention.

Pixel-related features which may be extracted from the images may be used as input for a classifier. For example, color values of the pixel and/or illumination or intensity values may be used as input features to the classifier. Typically, an image may be captured with R, G, and/or B values, which correspond to Red, Green and Blue channels of the image capturing device. The R, G, and/or B values of the pixel may be used as input features in the classification process of the image. In some embodiments, other pixel-related features may be extracted and used as input for a classifier, for example, the RGB values may be transformed to another color space, such as HSV or $YC_RC_V$.

Input to the linear classifier may include RGB values of pixels in the image. The x-axis of graph 200 may indicate, for example, the green component of the pixel, and the y-axis may indicate, for example, the red component of the pixel. Graph 200 may not be limited to two dimensions, and may include other pixel color components. For example a 3-dimensional graph may be construed, comprising the red, green and blue color components of the pixel. In some embodiments, the graph may be construed of other dimensions, e.g. components of different color spaces, such as HSV or $YC_RC_V$. Solid line 201 may indicate a separating plane (or in the two-dimensional case, a line). Each of points 205, 206 and 207 correspond to a pixel in the original image, with the corresponding color component values (e.g. red and green in this example). The exemplary points 205-207 in the graph 200 depict positive and negative classes, for example a "turbid content class" may be considered the positive class and a "tissue class" may be considered the negative class. A pixel with red and green values corresponding to point 205, for example, may be included in the positive class (e.g. the pixel is classified to depict turbid content) and its corresponding distance $d_1$ from the separating plane 201 may indicate the confidence level of the classification result (e.g. that the pixel belongs to the turbid content class). Similarly, point 207 may be included in the negative class (e.g. the pixel is classified to depict in vivo tissue), and its corresponding distance $d_3$ from the separating plane 201 may indicate, or correspond to, the confidence level that the pixel belongs to the tissue class.

The distances $d_i$ of points 205-207 from the separating plane 201, which may indicate a confidence level of the classification result for each point in the graph, may correspond to a probability of a pixel (represented by a point in the graph) to depict turbid content. For example, to calculate the probability of a pixel to depict turbid content, distances $d_i$ may be evaluated and trimmed to a predetermined range (e.g., all distances $d_i$ may be mapped to a value in the range between [−3, 3]), to obtain trimmed results. The trimmed results may then be normalized, for example mapped to values between zero to one, thereby obtaining a probability score for the pixels. In some embodiments, the scores may not be trimmed and/or may not be normalized.

Reference is now made to FIG. 3, which depicts a flow chart of a method for determining a turbid content score for an image, according to an embodiment of the invention. In operation 300, an input image may be received from an in vivo image stream. For example, a stream of images may be captured by imaging capsule 40, and an image may be received, for example by a data processor, for turbid content detection. In some embodiments, images from the image stream may pass several image processing detectors, one of which may be a content detector. In some embodiments all images from the stream may undergo a set (or a subset) of content detection operations. The images may be received, for example, via a receiving unit such as image receiver 12.

In operation 310, a portion of the image may be selected for content detection. The portion of the image may be referred to as a region of interest (ROI) in the image. For example, a predetermined mask or subset of the pixels in the image may be defined as the ROI, and pixels contained within the ROI may be selected for content detection. The selection of the subset of pixels belonging to the ROI may be related to properties of the imaging device. For example, pixels which are outside the optical focus of the imaging device, and/or pixels which are insufficiently illuminated due to illumination properties of the imaging device, may be excluded from the ROI. In some embodiments, content detection may be performed on the complete set of image pixels, and a ROI need not necessarily be selected.

In operation 320, a pixel content score or pixel probability for a plurality of image pixels may be calculated based on pixel properties, for example the pixel's RGB values. In some embodiments, the pixel content score may be calculated for all image pixels, while in other embodiments the pixel content score may be calculated for a selected portion or a subset of the image pixels. In some embodiments, the calculation may be performed only for a selected portion of the image pixels, e.g. a subset of pixels belonging to a ROI of the image. For example, if the imager 46 includes 320×320 pixels, the ROI may include a subset of N pixels, e.g. 256×256 pixels. Different portions of the image pixels may be selected, for example the ROI may include a circle truncated from an originally captured square image. In one embodiment the pixel content score or probability may be calculated according to for example the following equation (other equations may be used):

$$\text{pixel\_content\_score} = W_1 * \text{pixel}(R) + W_2 * \text{pixel}(G) + W_3 * \text{pixel}(B) + b$$

wherein:
  $W_1$ indicates a first scalar weight, used to multiply the Red component value of the pixel,
  $W_2$ indicates a second scalar weight, used to multiply the Green component value of the pixel,
  $W_3$ indicates a third scalar weight, used to multiply the Blue component value of the pixel, and
  b is a scalar value representing the bias of the function, which may be optionally added. The bias may not affect the performance of the content detector, and in some embodiments may be ignored or set to zero.

The pixel content score may be, indicate or correlate to a level of confidence, or the probability, that the pixel depicts or shows turbid content. The set of pixel content scores calculated for pixels of an image may be stored in a computer storage unit (e.g. storage unit 19 or a different storage unit), for example using an array structure, or a different data structure.

In some embodiments, pixels in the ROI may be classified as tissue pixels or content pixels based on the pixel content scores. Different classifiers may be used to classify pixels to content class or tissue class based on pixel properties. A classifier may be a linear classifier or a non-linear classifier. A linear classifier may produce faster results than a non-linear classifier, and in applications which require classification of a large amount of data in limited time, it may be advantageous to use linear classification. Thus, selection of a linear classifier may be more appropriate for classification of pixel values of images in an in vivo image stream. For example, linear classifiers are known to perform less overfitting on the training set and may produce a lower generalization error compared to non-linear classifiers.

A set of images may be provided as a training set for training a classifier. The training set may include a set of marked images, which contain areas (e.g. groups of pixels) marked as content and areas marked as depicting in vivo tissue. Each pixel in the image may be marked as content or tissue. The training set may also include a set of images which depict only tissue, and substantially no turbid content. The training set may include, for example 100 or more images which were marked by a health care professional such as physician or nurse. Marked images of the training set may include a classification for each pixel to one of two (or more) categories or classes, for example each pixel in the image may be marked either as a turbid pixel or a tissue pixel. In some embodiments, the classification may be provided for a portion of the image pixels and not for each pixel. In one embodiment, the images in the training set may include marked pixels which are statistically significant, e.g. pixels which clearly belong to one of the classes, and not borderline cases.

Other classes may be used, for example pixels may be classified as "lumen hole" pixels (e.g., the pixels are part of the dark lumen hole depicted in an image). Pixels may be classified as "pathology" pixels, e.g. depicting a specific pathology such as bleeding, or other types of pathologies which may be detected in an image. In some embodiments, the pixels may also be classified to a "white" class (based on color). Pixels which are mostly white may be part of bubbles or content found in the GI tract and depicted in an image, or part of a pathology (e.g. a head of an ulcer is typically whitish). Some training sets may include image with pixels which are classified to "no class" or unclassified, or pixels which belong to none of the other classes previously defined.

Based on the training set, a linear classifier may be determined. For example a linear classifier may be trained to provide a per-pixel probability of content based on the pixel' RGB values. The classifier may include a separating plane (e.g. separating plane 201 in FIG. 2), generated, for example, such that the margins (e.g. distances $d_i$) of the data values from the separating plane are maximal. In some embodiments, soft margins may be used. The soft margin is proportional to the Euclidean distance of the closest point on the separating plane. The larger the distance, the more certain the classifier is in its binary decision. Therefore the soft margins may be determined as a confidence level which can be translated into a probability estimation or a probability score of the pixel.

In some embodiments, a content threshold value may be determined for classifying a pixel as a content pixel or a tissue pixel. For example, based on analysis of the training set of marked images, a content threshold may be set to a scalar value. The pixel content score may be compared to the content threshold value, and a classification of the pixel as a content pixel or a tissue pixel may be obtained. In some embodiments, each pixel need not be classified as belonging to a certain class, e.g. a content pixel or a tissue pixel, since the content score may be sufficient to continue the content detection process.

In operation 330, the pixel content scores for an image may be sorted according to the pixel content score value, and arranged in a certain order, for example in an ascending order from least to greatest. Other arrangements are possible, for example descending order. The sorted scores may be stored, for example in a pixel content score array (with length N) in a storage unit, for example storage unit 19.

Images of a GI tract depicting turbid content may depict different levels or amounts of content. The amount or percentage of content depicted in the image may be considered when determining a content score for an image, and may be a factor in a decision whether to display an image to a reviewer or to exclude it from the displayed image stream. For example, the amount of content in a certain image may be 35% of the image (or of a ROI in the image). A content amount threshold P, which may correlate to a predetermined amount or percentage of content which may is depicted in an image, may be selected, for example preset to a value between zero to one or between 0-100, or may be user selectable.

The content amount threshold P may correspond to a maximal percentage of image pixels representing or depicting content, in images which may be classified as "sufficiently clean" images or images which may be selected for display in a reduced image stream. In some embodiments, the content amount threshold P may correspond to a maximal percentage of pixels from the image pixels (or percentage of pixels from the ROI pixels in an image) which are classified as content pixels. Different content amount thresholds may be selected, for example based on the training set, or according to health care professionals' preferences. In some embodiments the content amount threshold may be predetermined, while in other embodiments the content amount threshold P may be received as input by a user (e.g. by a health care professional who is reviewing the image stream). A main consideration in the selection of a content amount threshold is whether the image may represent or depict, in addition to the content, pathological tissue. When an image depicts substantially all content, e.g. an image which 95% or more of its pixels are classified as content pixels, it may be advantageous to exclude it from the displayed stream. In one example, the content amount threshold may be set to 95%. Other thresholds may be selected. The content amount threshold P may be set, for example based on the training set, to the largest amount or percentage of content found in an image which visibly depicts or represents pathology in addition to the turbid content.

Optionally, in some embodiments, a classifier may calculate the probability of an image to contain more than or equal or more than a threshold amount of turbid content.

In operation 340, the P-th percentile ($0 \leq P < 100$) of the N sorted scores of an image may be obtained, for example using the following set of operations (other sets of operations may be used):

(1) calculating the rank n:

$$n = \text{round}\left(\frac{P}{100} \times N\right)$$

wherein rounding the result may be performed for example to the nearest integer to obtain an integer rank, and (2) selecting the value out of the N sorted scores that corresponds to the obtained integer rank Other calculations of percentile may be used, for example weighted percentile.

The obtained value may be set as the image content score or rating for an image. For example, if P=95, and N=the number of pixels in a ROI of the image, the value corresponding to the $95^{th}$ percentile of the pixel content scores may be set as the image content score, and may later be used in a decision whether to display the image in a reduced image stream or to exclude it. In some embodiments, the $5^{th}$ percentile lowest pixel content score may be determined as the image content score.

In some embodiments, operation 330 is not essential. For example, the pixels need not be sorted, and a percentile of the array of pixel content scores correlating to the content amount threshold P may be calculated using other methods, e.g. by diving the pixel content scores to bins of a histogram, and selecting the bin which matches content amount threshold P.

Turbid content which may appear in an image may have different visual properties, for example different levels of transparency. Content may be partially transparent or semi-transparent, or may be substantially opaque. As a result of this visual property, when detecting turbid content, the stability of the detection results may vary. For example, if content detection is based substantially on comparing the pixel color and illumination properties to predetermined thresholds, the stability of the detection results may be impaired due to occurrences of borderline pixels which may receive a wrong classification by the classifier, for example, pixels which may have visual properties which are in close proximity to one or more classification thresholds. For example, images captured sequentially may have a high degree of similarity to each other. In case of a scene depicting, for example, semi-transparent turbid content, which may be captured across several sequential images, if the pixel visual properties (e.g., the pixel features) which are used in a classification process are close to the threshold level, alternating detection results may be generated by the classification algorithm. For example, in a first image of a set of sequential images, a classifier based on threshold levels (and not based on probability of content occurrence) may indicate that the image is a turbid image (e.g. depicts more than a threshold amount of intestinal content). However, in a sequential image, the classifier based on threshold levels may indicate that the image is not a turbid image (e.g., there is not a sufficient amount of intestinal content in the image to classify it as a turbid image). It would be advantageous to eliminate such detection (and mis-detection) fluctuations, and provide a content detector which produces more stable results for sequences of images or in vivo scenes. Selecting a percentile value of the pixel content score as the image content score may reduce such instability.

In some embodiments, optionally, a geometric distribution of the classified pixels in an image may be determined. The image content score may be modified according to the geometric distribution determination. For example, if the geometric pattern of the pixels classified as content pixels in an image are scattered throughout the image or the ROI, the image classification may be determined as a "tissue image", or the image content score may be modified to indicate that the confidence level of the image depicting at least the threshold amount of content is low (e.g. the image content score may be decreased). On the other hand, content pixels in an image may be determined to be geometrically arranged in conglomerated areas or may be clustered into masses in the image. One or more of these masses may consume an area in the image (or in the ROI) which may be larger than, for example, a predetermined size. Accordingly, the confidence level that the image depicts at least the threshold amount of content may increase, and the image content score may be modified accordingly, e.g. may be increased. To determine the geometric distribution of the pixels classified as content pixels, a set of morphological operations may be performed. For example, the morphological erosion operation may be performed, followed by the morphological dilation operation, in order to remove masses in the image suspected as content, which are smaller than a predetermined size. Alternatively, the geometric distribution of the pixels classified as tissue pixels may be determined, and similarly the confidence level that a portion of an image depicts tissue may increase accordingly.

In operation 350 a processor may select images from the original image stream for display to a user. The images may be selected based on the image content score or rating, in order to produce a reduced image stream in which images depicting substantially only content are excluded from display. For example, an image display threshold may be set, and images which have an image content score above the image display threshold may be selected for display in a reduced image stream. The image display threshold may be a predetermined value stored in a storage unit connected to the processor, or may be received as input from a user. Other selection methods may be used.

The selected images may be subject to additional filtering and selection operations, according to different editing filters which may be activated on the image stream. In some embodiments the content detection and image exclusion operations may be performed on a subset of images from the original image stream, e.g. on a reduced image stream which has already been filtered by other image processing operations.

In some embodiments, more than one type of content score may be calculated per image, and the decision whether to display an image in the reduced stream or to exclude it from display may be based on a condition or a set of conditions which must be fulfilled per each type of score. In some embodiments, the user may determine the amount or quality of images to be displayed or to be excluded from display. For example, the user may select to view only images which have less than 70% percent content, e.g. the $70^{th}$ percentile may be selected from the array N of sorted scores, or in some embodiments a condition may be checked if more than 30% of the pixels in the image or in a portion thereof are classified as content pixels. In another example, a user may select to view 75% of the images in the original stream. Accordingly, a processor may sort and arrange the images according to their image content score, and select for display only 75% of images which received the highest image content score. Other conditions or thresholds may be used, and may be predetermined and/or user-configurable.

Different sets or subsets of operations may be used. In some embodiments, only a subset of the operations may be performed. For example, some operations, e.g. 310, 330 or 350, may not be performed. In some embodiments, the pixels content score or image content score may be used for other operations or in other image selection processes.

Using a content detector to exclude from display images which depict more than a certain degree of content may result in a biased image stream when reviewed by a professional. For example, a health care professional who is reviewing the image stream may conclude that a content rating of the patient's procedure is quite clean, since the turbid content frames were removed from the image stream prepared for review. To avoid such misinterpretations of the reduced image stream, a percentage of frames removed during the content detection process from the original image stream may be calculated. In one embodiment, the percentage or amount of frames which were excluded by the content detector may be provided (e.g. displayed on a Graphic User Interface) to the image stream reviewer for example in each segment of the GI tract. In another example, a cleanliness index or content rating of the original image stream may be calculated based on the image content scores (e.g. a mean, average or weighted average of the image content scores), and may be displayed to the user. The content rating may for example provide a measure of the amount of content depicted in the captured image stream.

Figure 4:
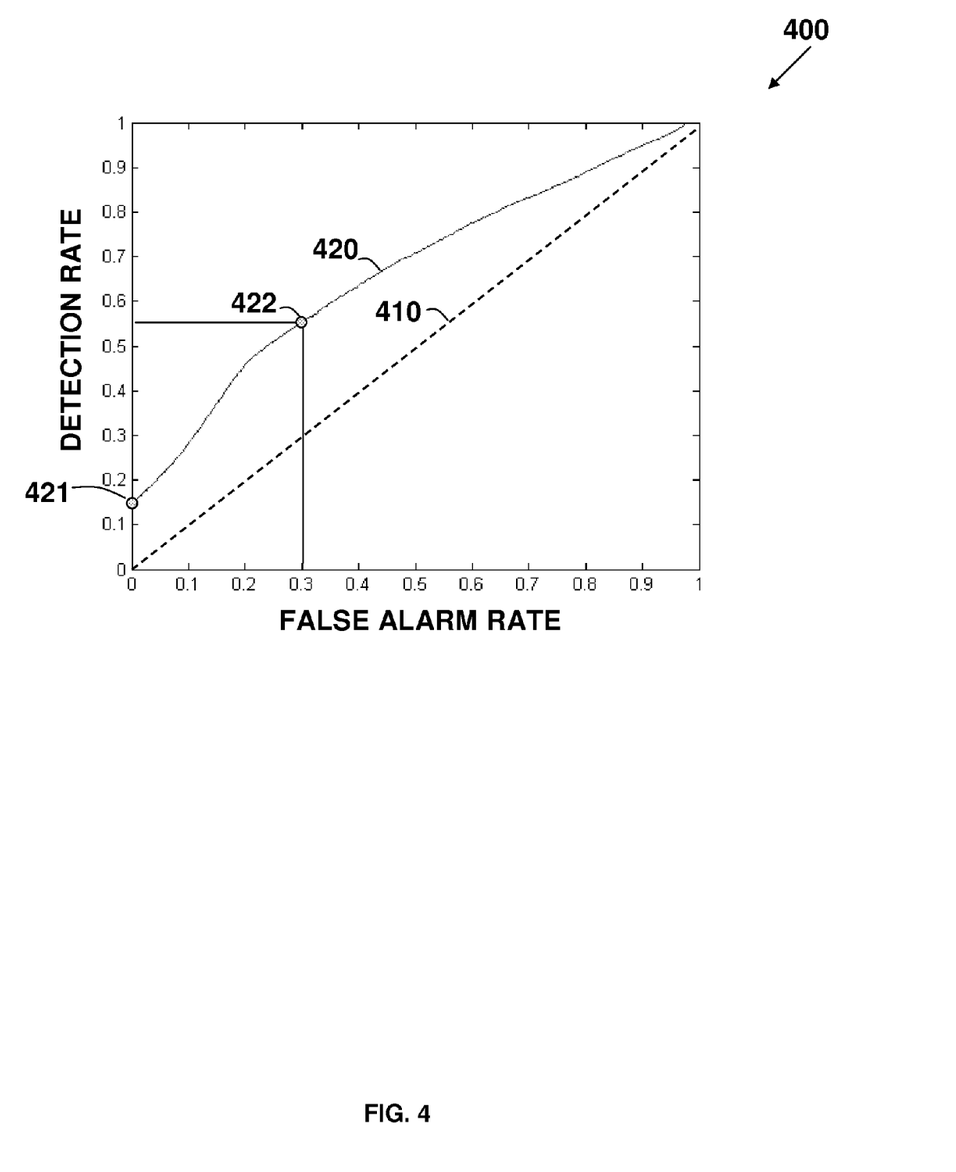

Reference is now made to FIG. 4, which illustrates an exemplary graph 400 of a ROC curve 420 generated for a content detector according to an embodiment of the invention. The ROC curve 420 is a graphical plot of the true positive rate vs. false positive rate, for a binary classifier system as its discrimination threshold is varied. The ROC curve indicates the sensitivity of the classifier. The x-axis of graph 400 may represent the rate of false alarms, e.g. the rate of false positive classifications of images by a content classifier. The false positive classifications may include images which were classified as content images and were excluded from the image stream, however depicted a sufficient percentage of pathological tissue, and should have been displayed to a user. The y-axis represents the rate of true positive classifications, or the set of images which were correctly classified as content and excluded from display in a reduced image stream.

Different operating characteristics may be selected for optimal operating conditions of the content detector. In some embodiments, it may be advantageous to select a configuration of the content detector such that no false positive classifications may be produced, e.g. corresponding to point 421 on the curve 420, in which x=0. In this configuration, no images which depict pathological tissue may be excluded from the reduced stream. However, this configuration enables exclusion of only 15% of the content images from the image stream. Other embodiments may allow a certain level of false positives, such configurations enable discarding a larger number of images from the stream (making the reduced stream shorter and thus quicker to review). For example, configurations corresponding to point 422 on curve 420, may allow a ratio of 30% false positives, and 55% true positives.

Embodiments of the invention may include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein.

Different embodiments are disclosed herein. Features of certain embodiments may be combined with features of other embodiments; thus certain embodiments may be combinations of features of multiple embodiments.

It will be appreciated by persons skilled in the art that the present invention is not limited to what has been particularly shown and described hereinabove. Rather the scope of the present invention is defined only by the claims, which follow:

The invention claimed is:

1. A method for detecting in-vivo content in images captured by an in vivo imaging capsule, the method comprising:
receiving an in vivo image captured by the imaging capsule;
calculating a pixel content score, per pixel, for at least a subset of the image pixels, wherein the pixel content score corresponds to a probability of the pixel to depict in vivo content; and
calculating an image content score based on the pixel content scores,
wherein the image content score indicates a probability that the image depicts more content than a threshold content amount and is calculated by selecting a pixel content score from the calculated pixel content scores corresponding to a content amount threshold percentile.

2. The method of claim 1 comprising calculating image content scores for a plurality of images and selecting, according to the image content scores, images for display in a reduced image stream.

3. The method of claim 1 comprising displaying a reduced image stream of the images captured by in vivo images.

4. The method of claim 1 comprising determining the content amount threshold based on a probability that an image includes a visible pathology.

5. The method of claim 1 comprising calculating an image stream content rating, wherein the content rating provides a measure of the amount of content depicted in the captured images, and displaying the image stream content rating to a user.

6. The method of claim 1 wherein the pixel content score is calculated based on the red, green and blue components of each pixel.

7. The method of claim 6 comprising training a linear classifier to provide pixel content scores based on a training set of images with pixels marked as content pixels.

8. A system for detecting in-vivo content in images, the system comprising:
a storage unit to store an image stream captured by an in vivo imaging capsule;
a processing unit to receive a plurality of images from the image stream,
and for each image to:
calculate a pixel content score for at least a subset of image pixels, wherein the pixel content score corresponds to a probability of the pixel to depict in vivo content, and calculate an image content score based on the pixel content scores, wherein the image content score indicates a probability that the image depicts more content than a selected content amount threshold calculated by selecting a pixel content score from the calculated pixel content scores corresponding to a content amount threshold percentile;
wherein the processing unit is to select images for display in a reduced image stream according to the image content score; and
a monitor to display the selected images of the image stream to a user.

9. The system of claim 8 wherein the processing unit is to select a subset of pixels in each image for calculating the pixel content score.

10. The system of claim 9 wherein the selection of the subset of pixels is according to a predetermined mask.

11. The system of claim 8 wherein the processing unit is to calculate an image stream content rating, wherein the content rating provides a measure of the amount of content depicted in the captured image stream, and wherein the monitor is to display the image stream content rating to a user.

12. A method for detecting in-vivo content in images captured by an in vivo imaging capsule, the method comprising:
receiving an in-vivo image captured by an imaging capsule;
for each pixel in at least a subset of the image pixels, calculating the probability the pixel represents in-vivo content; and
calculating an image content score based on the probability, wherein the image content score indicates a probability that the image represents more content than a threshold by selecting a probability from the calculated pixel probabilities, wherein the selected probability corresponds to a threshold percentile.

13. The method of claim 12 comprising calculating image content scores for a plurality of images and selecting, according to image content scores for the plurality of images, images for display in a reduced image stream.

14. The method of claim 12 comprising displaying the reduced image stream of the images captured by the in vivo device.

15. The method of claim 12 comprising determining the threshold based on a probability that an image includes a visible pathology.

16. The method of claim 12 comprising calculating an image stream content rating, wherein the content rating provides a measure of the amount of content depicted in the captured images, and displaying the image stream content rating to a user.

17. The method of claim 12 wherein the pixel probability is calculated based on
the red, green and blue components of each pixel.

18. The method of claim 12 comprising training a linear classifier to provide pixel probabilities based on a training set of images with pixels marked as content pixels.

* * * * *

UNITED STATES PATENT AND TRADEMARK OFFICE
CERTIFICATE OF CORRECTION

| | | |
|---|---|---|
| PATENT NO. | : 8,861,783 B1 | Page 1 of 1 |
| APPLICATION NO. | : 13/729263 | |
| DATED | : October 14, 2014 | |
| INVENTOR(S) | : Dori Peleg | |

It is certified that error appears in the above-identified patent and that said Letters Patent is hereby corrected as shown below:

Title Page

At Item (71): Delete "Given Imagine Ltd., Yoqneam (IL)" and insert --Given Imaging Ltd., Yoqneam (IL)--

Signed and Sealed this
Twenty-second Day of March, 2016

Michelle K. Lee
*Director of the United States Patent and Trademark Office*